US009724268B2

(12) United States Patent
Bertoni

(10) Patent No.: US 9,724,268 B2
(45) Date of Patent: Aug. 8, 2017

(54) METHOD FOR THE FILLING OF CONTAINERS WITH AUTOLOGOUS FRESH BLOOD COMPONENTS

(71) Applicant: Biomed Device S.R.L., Reggello (FI) (IT)

(72) Inventor: Marco Bertoni, Reggello (IT)

(73) Assignee: Biomed Device S.R.L., Modena (MO) (IT)

( * ) Notice: Subject to any disclaimer, the term of this patent is extended or adjusted under 35 U.S.C. 154(b) by 244 days.

(21) Appl. No.: 14/759,940

(22) PCT Filed: Jan. 9, 2014

(86) PCT No.: PCT/IB2014/058156
§ 371 (c)(1),
(2) Date: Jul. 9, 2015

(87) PCT Pub. No.: WO2014/108852
PCT Pub. Date: Jul. 17, 2014

(65) Prior Publication Data
US 2015/0342828 A1    Dec. 3, 2015

(30) Foreign Application Priority Data

Jan. 9, 2013  (IT) .............................. MO2013A0001

(51) Int. Cl.
  *B65B 31/04*    (2006.01)
  *A61J 1/20*    (2006.01)
  (Continued)

(52) U.S. Cl.
  CPC ........... *A61J 1/2058* (2015.05); *A61J 1/2062* (2015.05); *A61M 1/0209* (2013.01); *B65B 3/003* (2013.01); *A61M 1/0272* (2013.01)

(58) Field of Classification Search
  CPC ....... A61J 1/2058; A61J 1/2062; B65B 3/003; A61M 1/0209
  See application file for complete search history.

(56) References Cited

FOREIGN PATENT DOCUMENTS

DE    102008004977    7/2009
DE    202011004487    8/2012
(Continued)

OTHER PUBLICATIONS

International Search Report Dated May 19, 2015 From the International Searching Authority Re. Application No. PCT/IB2014/058156.

*Primary Examiner* — Jason K Niesz

(57) ABSTRACT

A method for the filling of containers with autologous fresh blood components, comprising the following phases of:
  a) providing an equipment (1) defining a transit channel (3) having at least a first gap (3a) associated with an empty syringe (4) or the like, at least a second gap (3b) associated with a bag (5) or the like containing an autologous fresh blood component and at least a third gap (3c) connected to a plurality of containers (6) to be filled;
  b) insulating the second gap (3b) from the third gap (3c) and placing in communication the first gap (3a) with the third gap (3c);
  c) suctioning the air contained in the containers (6) to be filled by means of said syringe (4) so as to define a vacuum inside them;
  d) insulating the first gap (3a) from the third gap (3c) and placing in communication the latter with the second gap (3b), the containers suctioning the contents of the bag (5) due to the effect of the vacuum defined inside them.

8 Claims, 2 Drawing Sheets

(51) Int. Cl.
*B65B 3/00* (2006.01)
*A61M 1/02* (2006.01)

(56) References Cited

FOREIGN PATENT DOCUMENTS

| | | |
|---|---|---|
| EP | 1930033 | 6/2008 |
| WO | WO 2011/095964 | 8/2011 |
| WO | WO 2012/123810 | 9/2012 |
| WO | WO 2014/108852 | 7/2014 |

METHOD FOR THE FILLING OF CONTAINERS WITH AUTOLOGOUS FRESH BLOOD COMPONENTS

RELATED APPLICATIONS

This application is a National Phase of PCT Patent Application No. PCT/IB2014/058156 having International filing date of Jan. 9, 2014, which claims the benefit of priority of Italian Patent Application No. MO2013A000001 filed on Jan 9, 2013. The contents of the above applications are all incorporated by reference as if fully set forth herein in their entirety.

TECHNICAL FIELD

The present invention relates to a method for the filling of containers with autologous fresh blood components such as, e.g., serum-eye drops, platelet-rich plasma, etc. . . .

BACKGROUND ART

Until now, autologous fresh blood components have been generally introduced inside specific vessels, of the micro test tube type, having relative closing caps, from which an operator then takes the desired quantity and introduces it inside a plurality of containers intended for use on the patient.

Because these operations require the transfer of the blood components from one container to another, and therefore their transit into the external environment, they must obviously be performed in a sterile environment. Furthermore, the preparation of such containers must be done by trained medical or nursing personnel inasmuch as the therapeutic effectiveness of the preparation is strongly affected by the quality and ways in which the aforementioned phases are performed.

It follows therefore that this known method of preparing containers with autologous fresh blood components besides being complicated to perform is also unsafe from a sanitary viewpoint and not therefore implementable on the basis of the applicable regulations on the subject. In fact, the correct performance of the operations described above is strictly correlated to the skills of the dedicated staff and to the environment where they are performed. These factors are highly restrictive inasmuch as they expose the preparation of the autologous blood component containers to various risks.

Another known method for the preparation of autologous blood component containers envisages filling a duct (dialysis infusate source) made of plastic material and closing such duct, e.g., by sealing in correspondence to a plurality of areas arranged in succession and spaced the one from the other, in such a way as to form a plurality of closed units.

These units are then opened, before being used, by cutting one of their respective extremities, e.g., using scissors, so as to make their contents available for use.

This second method for the preparation of units containing platelet-rich plasma also has several drawbacks.

More in particular, the units of known type are not easy and safe to use and do not allow compliance with the hygienic-health requirements of applicable regulations as well as of haemoderivative certification bodies.

In fact, the opening of such units by means of scissors or the like, results in residues of organic material contained in the relative unit remaining on the scissors cutting area, with the consequent risk of contaminating the contents of the other units subsequently cut with the same scissors.

This obviously involves the risk that the platelet contents of the units cut using already previously-used scissors will be polluted by the residues still on the scissors themselves, thereby negatively affecting their therapeutic properties and, above all, considerably increasing the risk of secondary infections in already immunodepressed patients and already debilitated organs.

SUMMARY OF THE INVENTION

The main aim of the present invention is to provide a method for filling containers with autologous fresh blood components which is practical and safe to use.

Within such aim, one object of the present invention is to provide a method for the filling of containers with autologous fresh blood components which allows complying with the hygienic-health requirements of applicable laws.

Another object of the present invention is to prevent any risk of external contamination of the blood components during transfer into the containers to be filled (aliquotation in closed system).

Yet another object of the present invention is, as far as possible, to separate the correct filling of the containers from the operator's skills and from the environment in which such filling is done.

Another object of the present invention is to provide a method for the filling of containers with autologous fresh blood components that allows to overcome the mentioned drawbacks of the background art in the ambit of a simple, rational, easy, effective to use and low cost solution.

The objects mentioned above are achieved by the present method for the filling of containers with autologous fresh blood components, according to claim 1.

BRIEF DESCRIPTION OF THE DRAWINGS

Other characteristics and advantages of the present invention will become more evident from the description of a preferred, but not sole, embodiment of an equipment for the performance of the method according to the invention, illustrated purely as an example but not limited to the annexed drawings in which.

DESCRIPTION OF SPECIFIC EMBODIMENTS OF THE INVENTION

Figure 1:
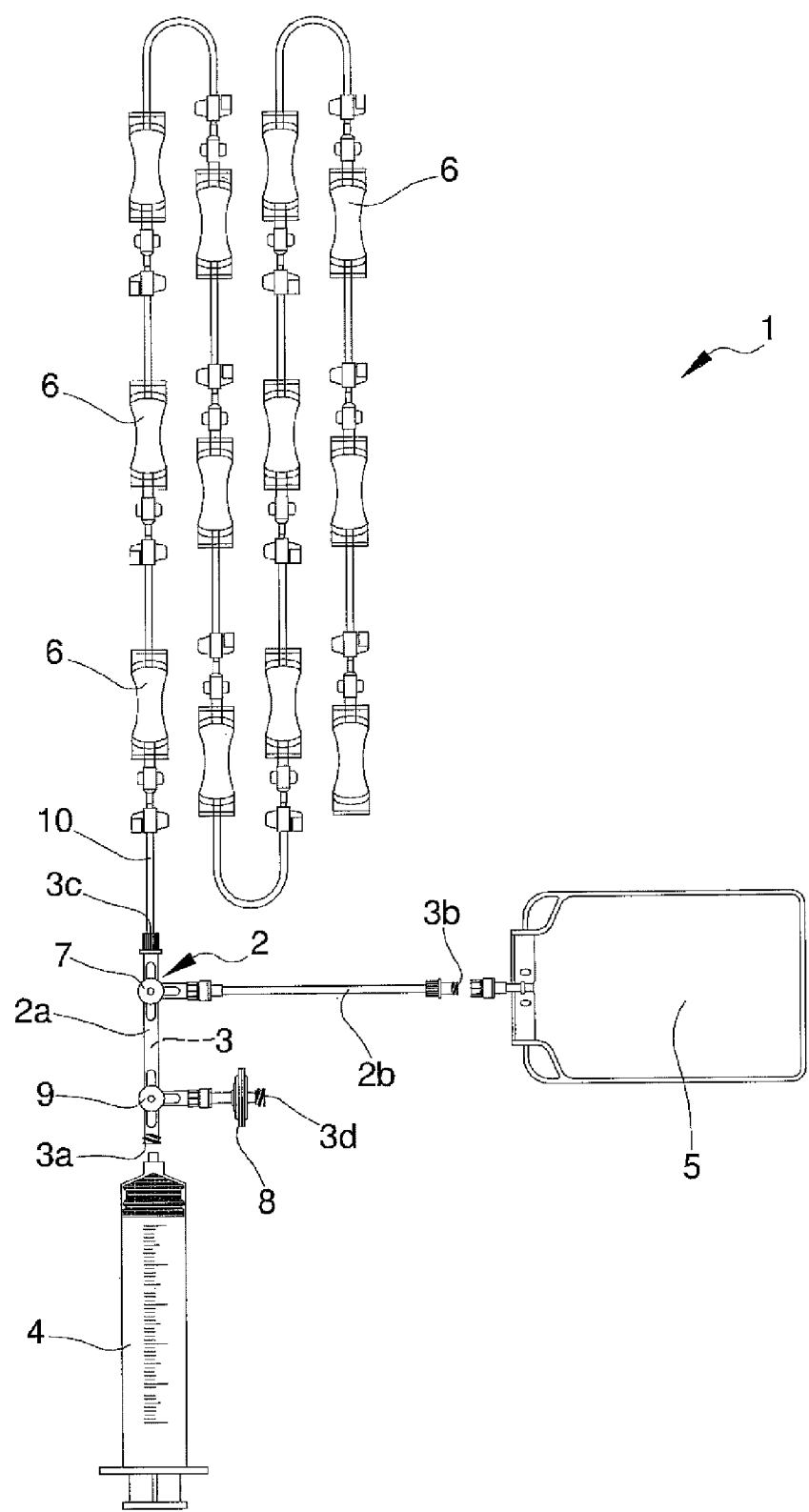
FIG. 1 is a plan view from above of an equipment for the performance of the method according to the invention, in a first embodiment.

With particular reference to such figures, globally indicated by 1 is an equipment for the filling of containers with autologous fresh blood components. The equipment 1 comprises at least a tubular element 2 which defines a transit channel 3.

The channel 3 has at least a first gap 3a associated with an empty syringe 4 or the like, at least a second gap 3b associated with a bag 5 or the like containing an autologous fresh blood component and at least a third gap 3c connected to a plurality of containers 6 to be filled. The bag 5 may also be replaced by another syringe.

More in detail, in the embodiments shown in the illustrations, the tubular element 2 has at least a main section 2a, from which extends at least a derivation 2b defining the second gap 3b.

Advantageously, the equipment 1 comprises first valve means 7 arranged along the channel 3 and which can be operated to selectively place the openings 3a, 3b and 3c in communication with each other.

More in detail, the first valve means 7 can be moved between at least a first configuration of use, wherein the first gap 3a is in communication with the third gap 3c and the second gap 3b is insulated, a second configuration of use, wherein the second gap 3b is in communication with the third gap 3c and the first gap 3a is insulated, and a third configuration of use, wherein the first gap 3a is in communication with the second gap 3b and the third gap 3c is insulated. The first valve means 7 are, e.g., of the three-way tap type.

Preferably, the channel 3 also comprises a further gap 3d communicating with the outside. More in particular, the further gap 3d is placed between the first and the second gaps 3a and 3b.

Suitably, the equipment 1 comprises a filtering element 8 inserted inside the further gap 3d and suitable for preventing impurities from entering inside the channel 3.

As can be seen in the illustrations, the equipment 1 also comprises second valve means 9 arranged along the channel 3 and which can be at least operated to put into communication/insulate the first gap 3a with/from the further gap 3d.

More in particular, the second valve means 9 are movable between at least a first configuration of use, wherein the first gap 3a is in communication with the further gap 3d and is insulated from the other gaps 3b and 3c, and at least a second configuration of use, wherein the further gap 3d is insulated from the other gaps 3a, 3b and 3c. The second valve means 9 can also have further configurations of use suitable for insulating the further gap 3d from the first gap 3a and placing it in communication, depending on the configuration taken on by the first valve means 7, with at least one between the second and the third gaps 3b and 3c. The second valve means 9 are also, e.g., of the three-way tap type.

In the first embodiment shown in the FIG. 1, the channel 3 has only a third gap 3c, with which is associated a supply duct 10 along which are arranged a plurality of containers 6 in series the one with the other.

Figure 2:
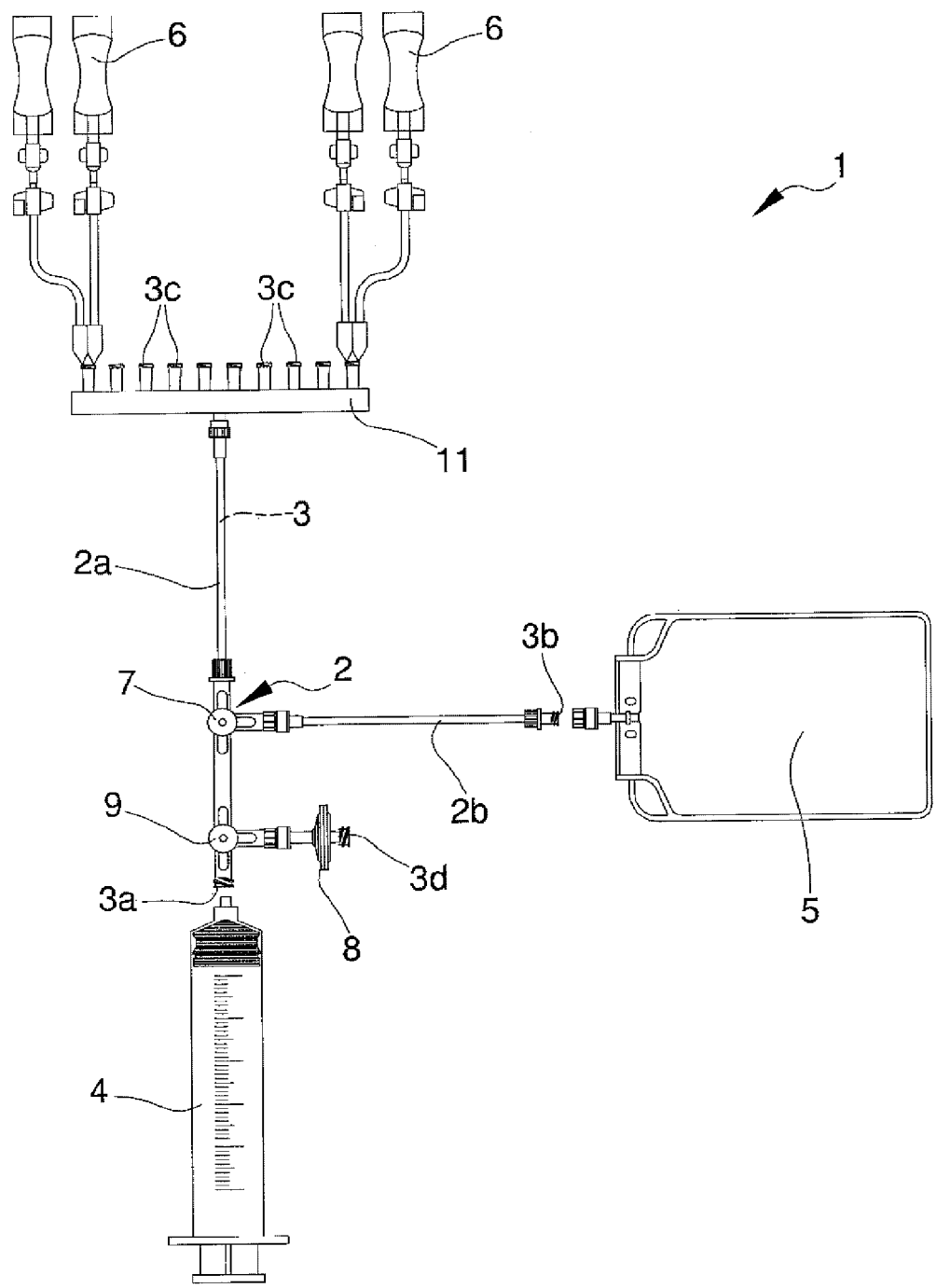
FIG. 2 is a plan view from above of an equipment for the performance of the method according to the invention, in a second embodiment.

In the second embodiment shown in FIG. 2, the tubular element 2 comprises a connecting element 11 which defines a plurality of third gaps 3c to which are connected the containers 6 to be filled.

The operation of the equipment 1 in the performance of the method according to the invention is described below.

Before proceeding to execute the phases required to fill the containers 6, it is obviously best to connect the empty syringe 4 to the first gap 3a and the bag 5, containing the blood component to be introduced into the containers themselves, to the second gap 3b.

The method forming the subject of the present invention first of all provides for the insulation of the second gap 3b from the first and from the third gaps 3a and 3c and the placing in communication of the first gap 3a with the third gap 3c. This phase is performed by intervening on the first valve means 7 and, more in particular, moving the relative three-way tap to the first configuration of use.

Suitably, in this phase, the second valve means 9 are operated so as to insulate the further gap 3d from the other gaps 3a, 3b and 3c.

After proceeding this way, the air contained in the containers 6 is suctioned by means of the syringe 4 to create the vacuum inside the containers themselves.

In the event of air remaining inside the containers 6, it is best to proceed with the following phases to complete the emptying of same. In particular, after removing the air by means of the syringe 4, the first gap 3a must be insulated from the second and from the third gaps 3b and 3c and the first gap itself must be placed in communication with the further gap 3d. This phase is performed by moving the second valve means 9 to the first configuration of use.

Subsequently, the air contained inside the syringe 4 is conveyed to the outside through the further gap 3d.

After emptying the syringe 4 of the air contained inside it, the second valve means 9 are again moved to the second configuration of use, so as to insulate the first gap 3a from the further gap 3d, and the above phases are repeated until the containers 6 are completely emptied.

Once the air has been removed from the containers 6, the first gap 3a is then insulated from the third gap 3c and the second gap 3b is placed in communication with the third gap itself. This phase is performed by moving the first valve means 7 to the second configuration of use.

At this point, the blood component contained in the bag 5 is suctioned by the containers 6 by effect of the vacuum created inside them.

More in detail, in the first embodiment, the substance contained in the bag 5 is introduced inside the channel 3 and enters inside the containers 6 passing through the third gap 3c. The containers 6 are then filled in succession following the introduction of the blood component contained in the bag 5 into the channel 3.

In the second embodiment shown in FIG. 2, on the other end, the substance contained in the bag 5 is introduced inside the channel 3 and enters, substantially at the same time, inside the containers 6 passing through the respective third gaps 3c.

In case of its being necessary to introduce a further quantity of the blood component contained in the bag 5 inside the containers 6, the first and the second gaps 3a and 3b have to be insulated from the third gap 3c and the first and the second gaps 3a and 3b must be placed in communication with each other, after which the contents of the bag 5 are suctioned by means of the syringe 4. This operation is performed by moving the first valve means 7 to the third configuration of use. During this phase, the second valve means 9 are arranged in the second configuration of use.

Subsequently, the first valve means 7 are again moved to the first configuration of use and the contents suctioned by the syringe 4 are conveyed towards the containers 6.

The phase of filling the syringe 4 with the contents of the bag 5 and the subsequent sending of such contents inside the containers 6 can be repeated until the containers themselves are completely full.

It has in practice been ascertained how the invention achieves the proposed objects and in particular, the fact is underlined that the method and the equipment forming the subject of the present invention permit easily and safely filling a plurality of containers with autologous fresh blood components.

In particular, the equipment according to the invention permits defining a closed and sterile path inside which the autologous fresh blood component is made to circulate and which, for this reason, permits preventing any type of external contamination.

Furthermore, the phases of the method forming the subject of the present invention permit very quickly and safely filling a plurality of containers and also make the success of such operations independent of the skills of the operator who performs them and of the environment in which the relative equipment is located.

What is claimed is:

1. Method for the filling of containers with autologous fresh blood components, wherein it comprises the following phases of:
   a) providing an equipment (1) defining a transit channel (3) having at least a first gap (3a) associated with an empty syringe (4) or the like, at least a second gap (3b) associated with a bag (5) or the like containing an autologous fresh blood component and at least a third gap (3c) connected to a plurality of containers (6) to be filled;
   b) insulating said second gap (3b) from said third gap (3c) and placing in communication said first gap (3a) with said third gap (3c);
   c) suctioning the air contained in said containers (6) to be filled by means of said syringe (4) so as to define a vacuum inside them;
   d) insulating said first gap (3a) from said third gap (3c) and placing in communication the latter with said second gap (3b), said containers suctioning the contents of said bag (5) due to the effect of the vacuum defined inside them.

2. A method according to claim 1, wherein it comprises, after the phase d), the following phases of:
   e) insulating said first and second gaps (3a, 3b) from said third gap (3c) and placing them in communication with each other;
   f) taking at least a part of the contents of said bag (5) by means of said syringe (4);
   g) insulating said first gap (3a) from said second gap (3b) and placing in communication the first gap itself with said third gap (3c);
   h) conveying the contents taken with said syringe (4) into said containers (6).

3. A method according to claim 1, wherein said equipment (1) comprises at least first valve means (7) that can be operated to place selectively in communication together said first, second and third gaps (3a, 3b, 3c).

4. A method according to claim 3, wherein at least the phases b) and d) and/or the phases e) and g) are carried out by intervening on said first valve means (7).

5. A method according to claim 1, wherein said transit channel (3) comprises at least a further gap (3d) communicating with the outside.

6. A method according to claim 5, wherein said further gap (3d) is placed between said first and second gaps (3a, 3b).

7. A method according to claim 1, wherein it comprises, after the phase c), the following phases of:
   c1) insulating said first gap (3a) from said second and third gaps (3b, 3c) and placing it in communication with said further gap (3d);
   c2) conveying the air taken by means of said syringe (4) to the outside through said further gap (3d);
   c3) insulating said further gap (3d) from said first, second and third gaps (3a, 3b, 3c) and repeating the phases c), c1) and c2) until said containers (6) to be filled are completely emptied.

8. A method according to claim 7, wherein it comprises second valve means (9) that can be operated at least to place in communication said first gap (3a) with said further gap (3d), insulating the first gap itself from said second and third gaps (3b, 3c), and to insulate said further gap (3d) from said first, second and third gaps (3a, 3b, 3c) and by the fact that the phases c1) and c3) are carried out by intervening on said second valve means (9).

* * * * *